(12) United States Patent
Pavlovic et al.

(10) Patent No.: US 6,635,882 B1
(45) Date of Patent: Oct. 21, 2003

(54) GANTRY SYSTEM AND METHOD FOR OPERATING SAME

(75) Inventors: Marius Pavlovic, Darmstadt (DE); Dieter Schardt, Darmstadt (DE)

(73) Assignee: Gesellschaft fuer Schwerionenforschung mbH, Darmstadt (DE)

( * ) Notice: Subject to any disclaimer, the term of this patent is extended or adjusted under 35 U.S.C. 154(b) by 0 days.

(21) Appl. No.: 09/889,209

(22) PCT Filed: Feb. 3, 2000

(86) PCT No.: PCT/EP00/00866
§ 371 (c)(1),
(2), (4) Date: Sep. 25, 2001

(87) PCT Pub. No.: WO00/45891
PCT Pub. Date: Aug. 10, 2000

(30) Foreign Application Priority Data

Feb. 4, 1999 (DE) .......................................... 199 04 675

(51) Int. Cl.[7] .................................................. H01J 3/26
(52) U.S. Cl. .................. 250/398; 250/396 R; 250/397; 250/492.3; 250/423 R
(58) Field of Search ................................ 250/398, 396, 250/400, 505.1, 396 R, 397, 423 R, 492.3; 378/12; 315/505, 500

(56) References Cited

U.S. PATENT DOCUMENTS 4,149,084 A * 4/1979 Arndt et al. ................. 250/492

OTHER PUBLICATIONS

"GSI Studies of a Gantry for Heavy–Ion Cancer Therapy" by Pavlovic, Marius, *The Journal of Jastro, The Official Journal of The Japanese Society for Therapeutic Radiology and Oncology*, vol. 9 Supplement Nov. 2, 1997. pp. 71–78.

* cited by examiner

*Primary Examiner*—Judy Nguyen
*Assistant Examiner*—Lam Nguyen
(74) *Attorney, Agent, or Firm*—Frommer Lawrence & Haug; Ronald R. Santucci (57) ABSTRACT

The invention relates to a gantry system for adjusting and aligning an ion beam onto a target from a freely determinable effective treatment angle. The ion beam therein is introduced in the horizontally arranged gantry rotation axis of the gantry system and is firstly deflected away from the gantry rotation axis by means of magnetic optics. The ion beam is then so aligned onto a target at adjustable angles of from 0 to 360° around the gantry rotation axis that the ion beam intersects the gantry rotation axis in the isocentre of the gantry system. Besides the gantry, the gantry system has a target carrier system having a rotatable target carrier, the carrier rotation axis of which is arranged in the isocentre in a vertical direction with the respect to the gantry rotation axis. The final deflection magnet so deflects the ion beam that the ion beam intersects the gantry rotation axis in the isocentre at an angle of between greater than or equal to 45° and less than 90°. Consequently, the ion beam can describe the surface of a cone when the gantry is rotated a full revolution about the gantry rotation axis. The target carrier system has a target carrier for each of two positions, which are perpendicular to one another in a vertical plane, it being possible to bring the carrier rotation axis into the isocentre of the gantry system. Furthermore, the invention relates to a method for irradiating a tumour from freely determinable effective treatment angles by means of the gantry system described above.

6 Claims, 6 Drawing Sheets

GANTRY SYSTEM AND METHOD FOR OPERATING SAME

The invention relates to a gantry system for adjusting and aligning an ion beam onto a target, according to the preamble of claim 1.

A gantry system of that kind is known from U.S. Pat. No. 4,870,287. In the case of the known gantry system, the ion beam is supplied to the gantry system in the horizontally arranged gantry rotation axis and is firstly deflected from the gantry rotation axis by means of magnetic optics.

The ion beam is then guided parallel to the gantry rotation axis by means of magnetic optics and, from that direction parallel to the gantry rotation axis, is finally deflected into a radial direction with respect to the gantry rotation axis. The target is generally arranged at the point of intersection of the radially directed ion beam with the gantry rotation axis. That point of intersection is defined as the isocentre.

Consequently, on one full revolution of the gantry about the gantry rotation axis, the ion beam can be aligned onto the target in a plane perpendicular to the gantry rotation axis and adjusted to angles between 0 and 3600°.

Besides the gantry, the gantry system comprises a target carrier system having a rotatable target carrier. The carrier rotation axis of the target carrier is arranged in the isocentre in a vertical direction with respect to the gantry rotation axis. Consequently, the gantry system, which comprises at least one gantry and one target carrier system, can so adjust and align an ion beam that a target arranged in the isocentre can be irradiated from a freely determinable angle in space. In the of a gantry system of that kind, it is necessary for the final deflection magnet of the gantry to deflect the ion beam by 90°, which is why a gantry of that kind is also referred to as a 90° gantry.

In the case of the 90° gantry known from the publication U.S. Pat. No. 4,870,287, therefore, the ion beam is, on leaving the gantry in the direction of the gantry rotation axis, perpendicular to the gantry rotation axis. An angle $\alpha$ of gantry rotation is defined between the plane in which the ion beam is guided through the gantry and the horizontal plane of the space in which the gantry rotation axis is located. A horizontal position of the gantry accordingly corresponds to either the angle $\alpha=0$ or the angle $\alpha=180°$ when the gantry is in the horizontal plane and consequently the ion beam is guided in the gantry in that horizontal plane. The uppermost position of the gantry in the vertical direction accordingly corresponds to the angle $\alpha=90°$ and the lowest position of the gantry has an angle of $\alpha=270°$.

A treatment angle $\gamma$ is defined between the horizontal plane of the space and the direction in which the ion beam enters a target volume. An effective treatment angle is defined between a frontal plane of a patient and the direction in which the ion beam enters a target volume. For a patient in a lying position, which is usual, the treatment angle and the effective treatment angle are identical.

In the 90° gantry system known from the publication U.S. Pat. No. 4,870,287, the target carrier is in the form of a table rotatable about a vertical axis and having a longitudinal axis and a transverse axis. An angle $\beta$ of target carrier rotation is defined between the longitudinal axis of the target carrier table and the gantry rotation axis. By virtue of the rotatability of the target carrier about a vertical axis, the angle $\beta$ can have values between 0° and 360°. For a prespecified treatment angle $\gamma$, which is dependent upon the gantry rotation angle $\alpha$, it is furthermore possible for a specific entry channel for tumour irradiation to be selected by adjusting the angle, of carrier rotation. By virtue of the adjustability of the angle $\beta$, which is associated with the target carrier rotation, and the adjustability of the angle $\alpha$, which is associated with the gantry rotation, it is possible in a conventional system, wherein the ion beam is deflected by the final deflection magnet in a radial direction with respect to the gantry rotation axis, for the target volume fixed on the target carrier to be aligned for any entry channel for the purpose of tumour treatment.

The 90° gantry system known from the publication U.S. Pat. No. 4,870,287 has the disadvantage that the final deflection magnet of the gantry must deflect the ion beam through at least 90° in order to make possible all treatment angles $\beta$ in a gantry system having a target carrier system. The large deflection angle of the final deflection magnet necessitates, depending upon the mass number of the ions to be deflected, a large radius or a high magnetic field strength. Associated with that is the disadvantage that, on the one hand, a gantry has hitherto been successfully constructed only for ions having the smallest mass number, that is to say for protons; for ions having a higher mass number of between 4 and 16 the final deflection magnet inflates the scale and mass of the gantry to such an extent, because of the heavy ions having a mass number higher than a proton, that a gantry system is no longer appropriate for clinical use.

In order to reduce the mass and volume of a gantry for ions that are heavier than protons, proposals exist for the use of super-conducting materials for the exciting coils of the deflection magnets. Although the masses to be rotated and the volume of the gantry would be reduced as a result, the costs for cooling the super-conducting materials would make the gantry system considerably more expensive, especially as 360° rotation is extremely problematic for a cooling system using liquid helium or liquid nitrogen for modern super-conducting materials.

A further proposal, presented in the Japanese publication Journal of the Japanese Society for Therapeutic Radiology and Oncology, vol. 9, suppl. 2, November 1997 as part of the Proceedings of the XXVII PTCOG Meeting by M. Pavlovic under the title "GSI Studies of a Gantry for Heavy Ion Cancer Therapy", enables the mass and volume of the gantry to be reduced by changing the degree of deflection of the final deflection magnet from, formerly, 90° to 60°. That solution has the disadvantage that it is possible to achieve a treatment angle $\gamma$ of only from 0° to 60° by means of a so-called 60° gantry of that kind in conjunction with the conventional target carrier system. Consequently, it is no longer possible to achieve treatment angles $\gamma$ of between greater than 60° and 90° by means of a gantry system of that kind, which has a deflection angle of 60° for the final deflection magnet.

The problem of the invention is to provide, by means of a gantry having a reduced deflection angle of the final deflection magnet, a gantry system according to the preamble of claim 1 that does not require super-conducting materials for the magnetic optics and that, despite reducing the deflection angle of the final deflection magnet to below 90°, allows an ion beam to be adjusted and aligned onto a target from a freely determinable effective treatment angle. The problem of the invention is furthermore to provide a method for irradiating a target volume and adjusting and aligning an ion beam for treatment of a tumour using the gantry system according to the invention.

That problem is solved by the features of the subject matter of claims 1 and 60.

For that purpose, the final deflection magnet so deflects the ion beam that it intersects the gantry rotation axis in the isocentre at an angle of between greater than or equal to 45° and less than 90°, so that the ion beam describes a surface of a cone on rotation of the gantry through a full revolution about the gantry rotation axis, and the target carrier system has a target carrier for two positions, which are perpendicular to one another in a vertical plane, the carrier rotation axis of which target carrier can be brought into the isocentre of the gantry system. Such a solution has the advantage that the target carrier has to be fixable only in two specific positions and, in both positions, which are perpendicular to one another in a vertical plane, has to be rotatable about a vertically aligned carrier rotation axis. A significant advantage of this gantry system is that even angles that are less than 90° and preferably less than 60° and that therefore advantageously make possible an extremely low gantry volume and extremely small dimensions for the diameter of a gantry can be achieved by means of the gantry system according to the invention. Such a compact gantry system does not require expensive auxiliary equipment for cooling super-conducting materials. A further advantage of such a gantry having conventional magnetic optics is that it is now also possible for ion beams of ions that are heavier than protons, having mass numbers of between 4 and 16, to be adjusted and aligned for any freely determinable effective treatment angle by means of a gantry system that is suitable for clinical conditions.

In order to irradiate a target volume with an optimum dose distribution, there is preferably provided, in the case of the gantry system according to the invention, a deflection means for the ion beam in order to scan the target volume layer by layer therewith. The ion beam is preferably guided in the gantry, from the coupling-in point of the ion beam into the gantry rotation axis to the deflection of the ion beam in the final deflection magnet of the gantry system, by first deflecting the ion beam away from the gantry rotation axis using a 38° deflection magnet and by bringing it into a direction parallel to the gantry rotation axis using a second 38° deflection magnet. In that parallel direction, the ion beam passes through two scanner magnets, which deflect the ion beam in two directions oriented perpendicular to one another (horizontal and vertical with respect to the ion beam) and orthogonal to the ion beam, so that scanning of a surface of the target volume is advantageously made possible after the scan-deflected ion beam has passed through the final deflection magnet.

The preferred positioning of the scanning system upstream of the final deflection magnet accordingly reduces the gantry radius considerably and requires, however, an enlarged aperture in order to allow a large treatment area. That preferred arrangement of deflection magnet and scanning systems exhibits a high degree of ion-optical flexibility. The ion beam in the isocentre can therefore be modified advantageously from 2 to 16 mm diameter and the magnetic optics of the gantry are always achromatic.

In a preferred embodiment of the invention, the final deflection magnet so deflects the ion beam that the gantry rotation axis is intersected in the isocentre at an angle of greater than or equal to 45° and less than 60°. The deflection angles of below 60° especially show the enormous advantages of the present invention in that, on the one hand, the gantry dimensions are minimised and, on the other hand, the gantry system in the combination of the preferred embodiment of the gantry with the target carrier system according to the invention ensures that an ion beam can be adjusted and aligned onto a target from a freely determinable effective treatment angle.

In a preferred embodiment of the invention, the target carrier system has a revolving platform, which is rotatable about a vertical revolving platform axis. Arranged on that revolving platform are two target carriers in two positions, the positions being perpendicular to one another in a vertical plane. Each of the two target carriers is rotatable about a vertical carrier rotation axis.

That preferred target carrier system allows for a patient to be arranged in either a lying or a sitting position on the target carrier, depending upon the effective treatment angle. For medical reasons, the effective treatment angle must be a freely determinable angle in the patient co-ordinate system in order to ensure as far as possible optimum scanning of the target volume by the ion beam.

Optimisation of the ion beam dose distribution in the target volume or in a volume element of the target is substantially dependent upon the structure of the healthy tissue on top of the tumour volume, through which healthy tissue radiation has to pass. The medical determination of the effective treatment angle and entry channel accordingly has to take appropriate account of tissue cavities and densifications of tissue, for example in the case of bone tissue, as well as the location of critical organs in the vicinity of the tumour. In that regard, a freely determinable effective treatment angle, which is made possible by the gantry system according to the invention, is a great advantage for clinical treatment.

The vertical carrier rotation axes of the two positions of the target carriers can preferably be brought alternately into the isocentre of the gantry system by means of a revolving platform as a result of rotation of the revolving platform about its revolving platform axis. This preferred embodiment is associated with the advantage that the patient can be positioned in one of the two positions on the appropriate target carrier and can then be brought on the target carrier into the isocentre of the gantry system by means of the revolving platform. The gantry can then be adjusted to the previously determined angle a and the target carrier in the selected position can be adjusted to the predetermined angle β by means of a rotary movement about the vertical carrier rotation axis. After those three adjustments, the target volume can then be scanned with the scan-deflected ion beam.

In a further preferred embodiment of the invention, the target carrier system has two separate delivery rails, on each of which there is arranged one target carrier of the two positions, the delivery rails being capable of laterally displacing, from different directions in each case, either of the target carriers with its rotation axis into the isocentre alternately. That system has the advantage that the patient can be positioned and prepared on the selected target carrier outside the isocentre and can then be brought into the isocentre by displacement on the delivery rails. In the isocentre, the target volume can be scanned if in the meantime the gantry rotation angle α has been adjusted by rotation of the gantry and β has been adjusted by rotation of the target carrier.

In another preferred embodiment, the target carrier system has a universal robot system, which arranges the target carrier in two positions and arranges the vertical carrier rotation axes in the isocentre. Such multi-axis robot systems enable a rotatable target carrier to be arranged in different positions in the isocentre and consequently replace the two target carriers of disparate construction that are otherwise necessary as well as any delivery rails or revolving platforms. Such a universal robot system can, for this preferred application, be greatly simplified, especially because only two positions located perpendicular to one another in the vertical plane are required for the rotatable target carrier.

The method for irradiating a tumour from a freely determinable effective treatment angle by means of a gantry system is characterised by the following method steps:

a) determining the most advantageous effective treatment angle and the most advantageous entry channel with respect to the location and size of a tumour in healthy tissue and with the requirement for minimum exposure of the surrounding tissue to radiation together with optimum distribution of an ion beam dose for the tumour tissue to be irradiated, b) selecting, from two positions located perpendicular to one another in a vertical plane, the target carrier position required for the determined effective treatment angle, c) bringing the carrier rotation axis of the suitable target carrier position into the isocentre of the gantry system, d) aligning and adjusting the target carrier by rotation of the target carrier about its vertical carrier rotation axis in respect of the most advantageous angle, e) aligning and adjusting the gantry by rotation of the gantry about its horizontal gantry rotation axis in respect of the most advantageous angle, f) spatially scanning the entire tumour volume, by means of the ion beam, from the effective treatment angle.

This method has the advantage that, by means of the combination of a gantry system that is limited to treatment angles γ and a target carrier system that delivers the target to the gantry isocentre in two positions located perpendicular to one another in a vertical plane, any freely determinable effective treatment angle can be adjusted for irradiating the tumour volume so that a target can be irradiated with ions without restricting the effective treatment angle. In this context it is immaterial whether the angle α is first adjusted by means of the gantry and then the angle β is adjusted by means of the target carrier or whether the reverse order is selected.

It is merely of significance that for effective treatment angles of from 0 to 90° minus λ only one position and therefore, preferably, one of the target carriers can be used and for angles between 90° minus λ and the deflection angle λ of the final deflection magnet both positions of the target carrier can be utilised and for effective treatment angles between the deflection angle of the final deflection magnet and 90° the other of the two positions for the target carrier can be employed. The fundamental advantage of this method is consequently that, despite the final deflection magnet having a restricted deflection angle, the tumour to be treated can be treated with an ion beam from any freely determinable direction and therefore the medically optimal irradiation direction can be achieved by means of a gantry system of reduced mass, volume and cost.

Further advantages, features and possibilities for use of the invention are illustrated below using exemplary embodiments with reference to the annexed drawings.

Figure 1:
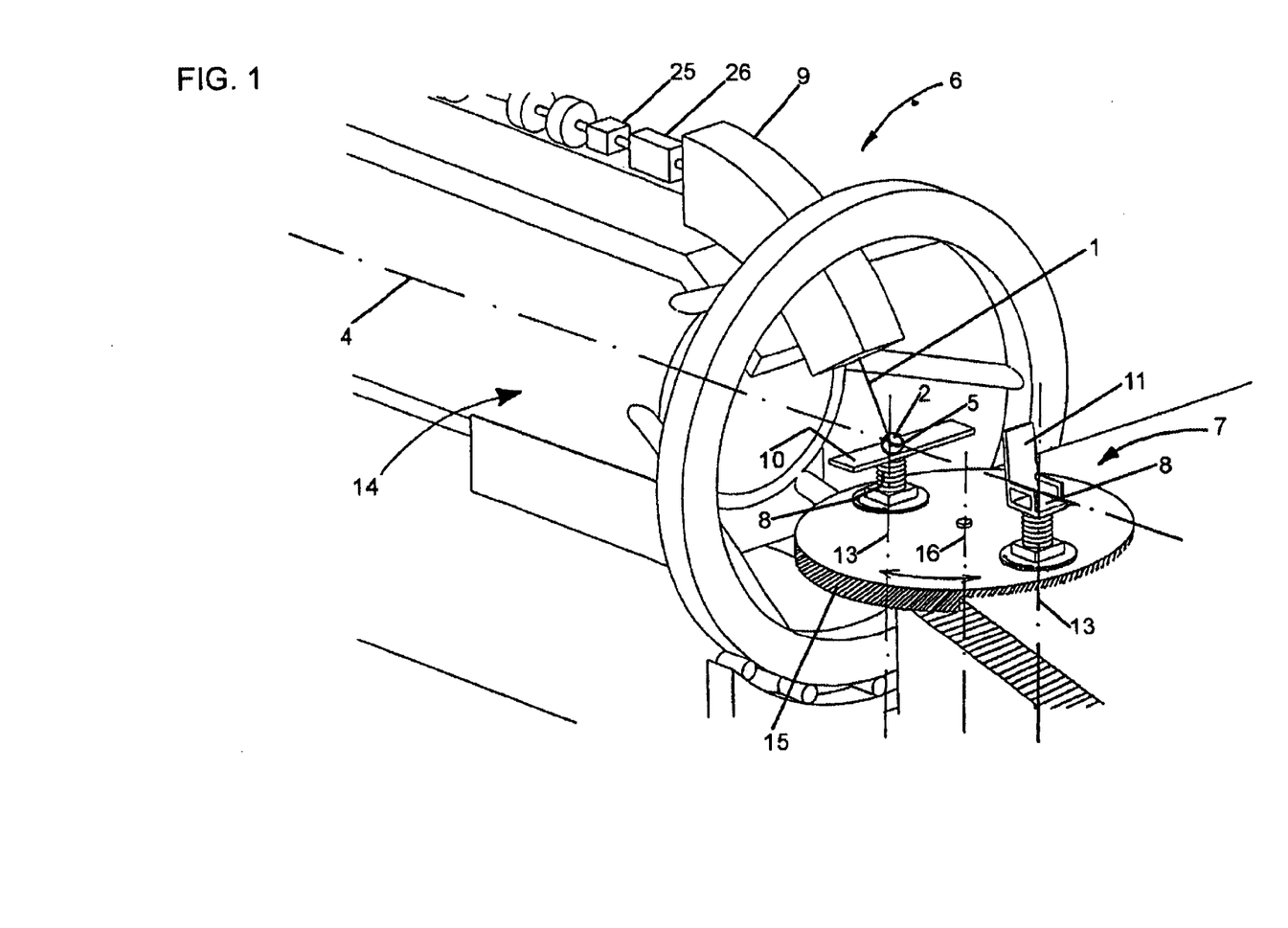
FIG. 1 is a perspective view of an embodiment of the gantry system according to the invention.

FIG. 1 is a perspective view of an embodiment of the gantry system 6 of the invention. Such a gantry system 6 directs an ion beam 1 onto a target 2. For that purpose, the ion beam 1 is supplied to the gantry system 6 in the horizontally arranged gantry rotation axis 4 and, by means of magnetic optics, is firstly deflected from the gantry rotation axis 4 and then guided parallel to the rotation axis of the gantry system. The gantry 14 can perform a full revolution through an adjustable angle α of from 0 to 360°. During such a revolution the ion beam describes the surface of a cone, the tip of which lies on the gantry rotation axis and intersects the gantry rotation axis in the isocentre 5. The gantry system 6 has a target carrier system 7 in addition to the gantry 14. This target carrier system 7 has at least one rotatable target carrier 8, the axis of rotation 13 of which can be arranged in the isocentre in a vertical direction with respect to the gantry rotation axis 4.

The final deflection magnet 9 so deflects the ion beam 1 that it intersects the gantry rotation axis 4 in the isocentre 5 at an angle of between greater than or equal to 45° and less than 90°. In the illustrated embodiment, that deflection angle is 55° so that the ion beam 1 describes the surface of a cone having an angle of opening of 110° when the gantry system 6 is rotated through a full revolution about the rotation axis 4. In FIG. 1, the angle α has been adjusted to 90° so that the ion beam deflection system of the gantry 14 is arranged in its uppermost position. A target 2 arranged on the target carrier 8 in the position 10 can be rotated about a vertical axis 13 in the isocentre and, despite the gantry having the possibility of complete revolution from 0 to 360°, can be irradiated only up to treatment angles corresponding to the exit angle of the ion beam from the magnetic optics of the gantry. In the embodiment having a 55° gantry, that exit angle is 55° with respect to a horizontal plane because the ion beam is deflected only by that 55° from a line parallel to the gantry rotation axis by means of the final deflection magnet 9.

With a target carrier 8 in position 10 it is therefore not possible to achieve all effective treatment angles. This preferred embodiment of the invention therefore has a further target carrier 8 which makes possible a second position 11 for the target, that position 11 being aligned perpendicular to position 10 in a vertical plane. In that position 11, the target can be acted upon at the effective treatment angles that are not achievable in position 10, that is to say at effective treatment angles of from 55° to 90°. Furthermore, effective treatment angles of from 35 to 550 can be achieved with both positions 10 and 11 of the target carrier 8.

It is consequently possible, by means of this embodiment, to adjust an ion beam and to align it onto a target, that ion beam hitting the target from a freely determinable effective treatment angle despite the final deflection magnet 9 having a reduced deflection angle.

The entire target volume can be scanned volume element by volume element and layer by layer by means of a scannable magnetic horizontal deflection means 25 arranged upstream of the final deflection magnet 9 and a scannable magnetic vertical deflection means 26 arranged between the horizontal deflection means 25 and the final deflection magnet 9. That scanning is carried out layer by layer by means of the fact that the particular energy of the ion beam adjusts the depth of penetration and, therefore, the height of the layer in the target.

As a result of appropriate programming of the horizontal deflection means 25 and vertical deflection means 26, a very wide variety of target volume forms can be scanned and, as a result, tumour tissue can be differentiated from surrounding healthy tissue with razor sharpness.

By virtue of the increased mass moment of inertia of ions that are heavier than protons, a gantry system having an exit angle after the final deflection magnet of less than 90° has the advantage that the gantry system according to the invention can be constructed with a significantly smaller radius than a conventional system which requires deflection of 90°.

Figure 2:
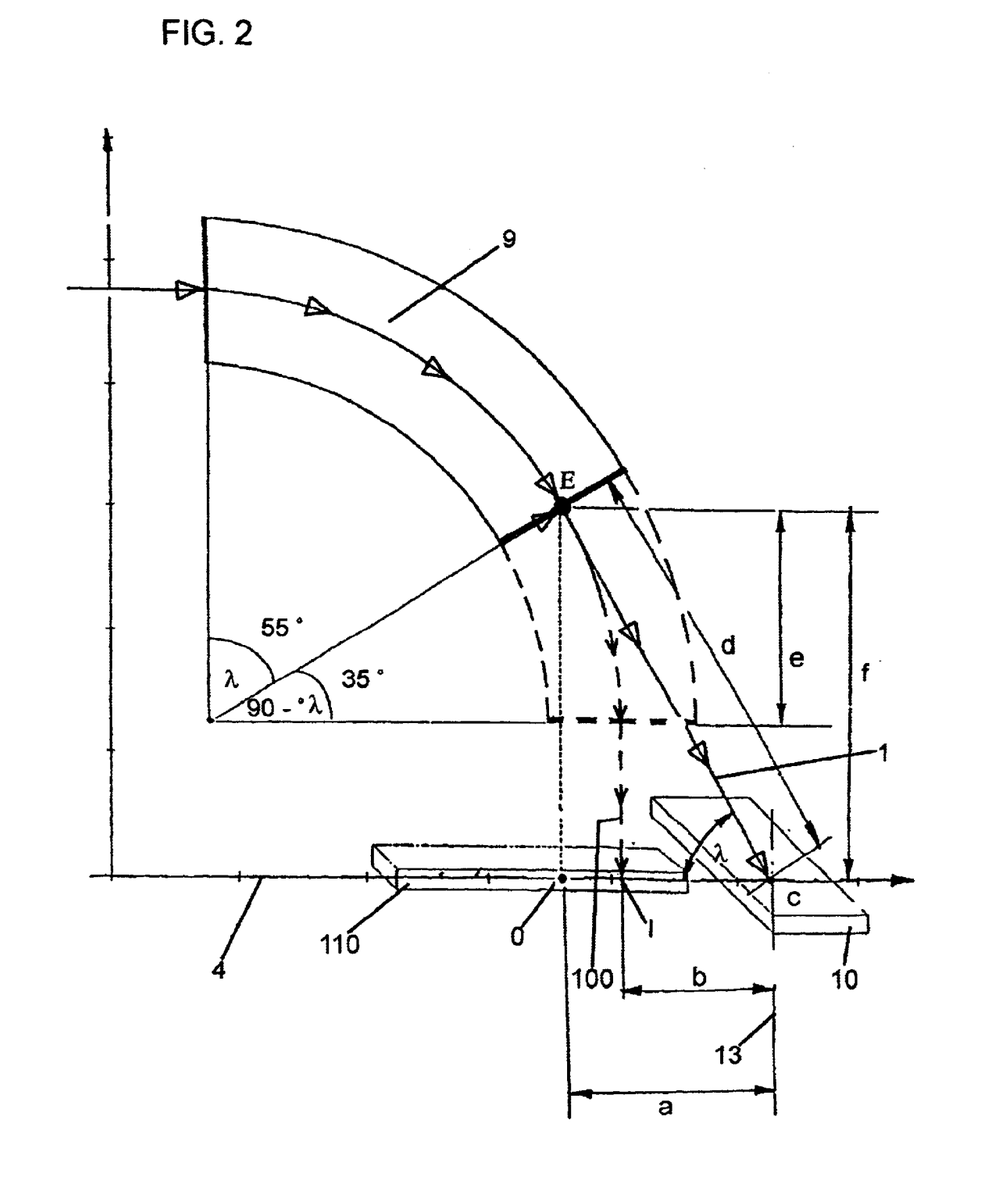
FIG. 2 shows a comparison between the action of the final deflection magnet of a conventional gantry and that of a gantry used in the gantry system according to the invention.

This difference is clearly shown by a comparison in FIG. 2 illustrating the action of a final deflection magnet of a conventional 90° gantry and that of, for example, a 55° gantry used, for example, in a preferred embodiment of the gantry system.

In the prior art of a 90° gantry, which hitherto has been suitable only for protons, the final deflection magnet deflects the ion beam 100 from a direction parallel to the gantry rotation axis 4 into a radial direction with respect to the gantry rotation axis 4 and hits the target at an adjustable angle α of between 0 and 360° according to the angle of rotation of the gantry and, by rotating the target carrier 110, it is possible to adjust almost any angle in space for irradiation of the target.

In this exemplary embodiment, with an exit angle from the final deflection magnet 9 at point E, the treatment angles γ are limited to 0° to 55°. In this case, compared to a 90° gantry, the isocentre 5 moves outside the gantry from point I to point C, a considerable distance b along the gantry rotation axis 4, and at the same time the size of the final deflection magnet is considerably reduced so that either the volume of the entire gantry can be reduced or the radius available for the target carrier 8 and the patient to be treated can be increased by a distance l to a clear space of radius r. In fact, the space gained by reducing the deflection angle of the final deflection magnet 9 is used for reducing the overall size of the gantry system.

Figure 3:
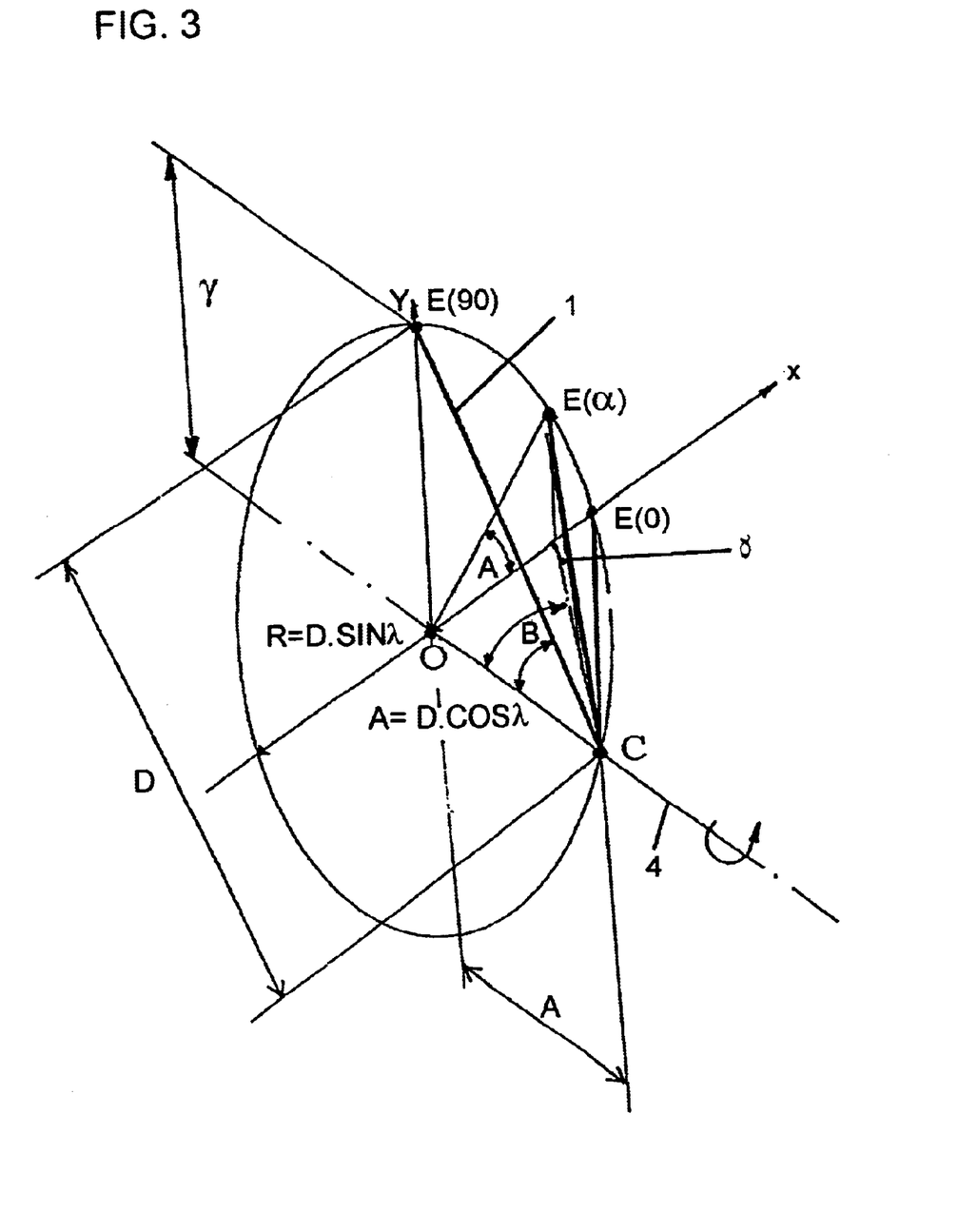
FIG. 3 shows the angular relationships and the definitions of angles for a gantry as they are used in the gantry system according to the invention.

FIG. 3 shows in that regard the angular relationships and the definitions of angles for a gantry as they are used in the gantry system according to the invention. In that regard the line 4 symbolises the gantry rotation axis, which together with the X axis fixes a horizontal plane. The ion beam, which emerges at point E, intersects the gantry rotation axis at point C, the isocentre 5.

FIG. 3 shows three positions of the gantry and the exit point E: firstly when the deflection system for the ion beam is in its uppermost position, that is at E (90); then at a desired angle α at E (α); and finally in a horizontal plane at E (0). Whereas the angle α can be adjusted by rotation of the gantry about its gantry rotation axis, the angle β is adjusted by rotation of the target carrier in a vertical direction with respect to the gantry rotation axis, the carrier rotation axis likewise passing through the isocentre 5 at point C.

The angle λ is prespecified by the final deflection magnet and remains unchanged on all rotary movements of both the gantry rotation axis and the carrier rotation axis. The treatment angle γ and the entry channel through which the beam penetrates into the patient are produced by the combination of the two rotary movements, of the gantry and of the target carrier. The treatment angle γ is always less than or equal to λ and the effective treatment angle is accordingly limited to one of the two positions of the target carrier. If, however, the target carrier occupies the second position, which is displaced through 90° in the vertical plane, the effective treatment angle for the target can be adjusted to the effective treatment angles in the first position. The spacing d between the exit point E and the isocentre 5 at point C simultaneously determines in conjunction with the angle λ described above the length a by which the isocentre projects out from the gantry and also the possible clear space of radius r that is available for the equipment for treating a patient in the gantry system according to the invention.

Figure 4:
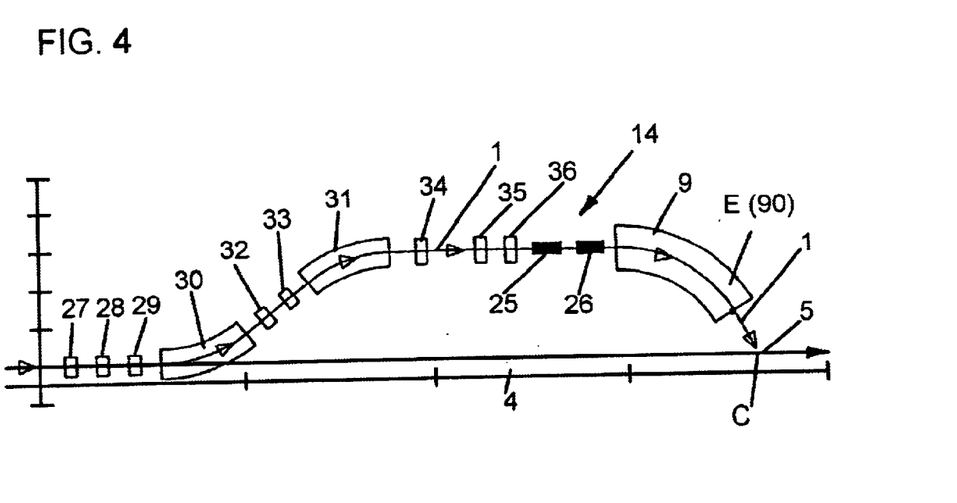
FIG. 4 shows the ion beam guidance of the gantry when α=90°.

FIG. 4 shows the guidance of the ion beam 1 of the gantry when α=90°, that is to say in the uppermost position of the deflection magnets. This gantry was designed for a 55° exit angle, the implementation specifications having been so selected that an isocentric construction is made possible and, at the same time, scanning of the target volume in two active directions, that is to say layer by layer, is made possible, so that this embodiment essentially has the following advantageous properties and arrangements:

1. achromatic beam optics,
2. modifiable beam size from 4 to 16 mm in steps of 1 mm,
3. a maximum beam energy of 400 MeV/u for a carbon ion beam having a depth of penetration into water of 27 cm,
4. a scanning field of size 20×10 cm$^2$,
5. a scanning mode of low angular deviation, that is to say the angle between the impinging scanning beam and the perpendicular to the surface being scanned is less than 1°,
6. a narrowing of the beam is located in the isocentre, that is to say the narrowing of the beam in the isocentre has the advantage that the beam circumference changes only very slightly in the vicinity of the narrowing so that, as a consequence, variations in beam width can be disregarded within a limited tumour volume, and finally
7. a minimum run from the gantry exit to the isocentre of 1.2 m.

A suitable arrangement of such a beam transport system having the above construction features is shown in FIG. 4. This gantry 14 consists of a straight adaptation region, in which the ion beam is introduced in the gantry rotation axis 4. That entry adaptation region consists of three quadrupoles 27 to 29. There is then a shoulder bend comprising two 38° deflection magnets 30 and 31 with two quadrupoles 32, 33 located between them; an upper straight region, in which the ion beam is guided parallel to the gantry rotation axis 4, having three further quadrupoles 34 to 36 and two scanning magnets with horizontal 25 and vertical 26 deflection means for scanning the target volume; and a final 55° deflection magnet having a large aperture.

The clear space for the patient has a radius of about 1.2 m, the outer radius of the gantry is about 2.8 m. Essentially, the size of the beam is advantageously determined mainly by the first three quadrupoles arranged in the curve-free region of the entry region. Such an arrangement exhibits a high degree of ion-optical flexibility. The beam in the isocentre can be of narrowed diameter from 2 to 16 mm and the optics of the gantry always perform in an achromatic state.

Figure 5:
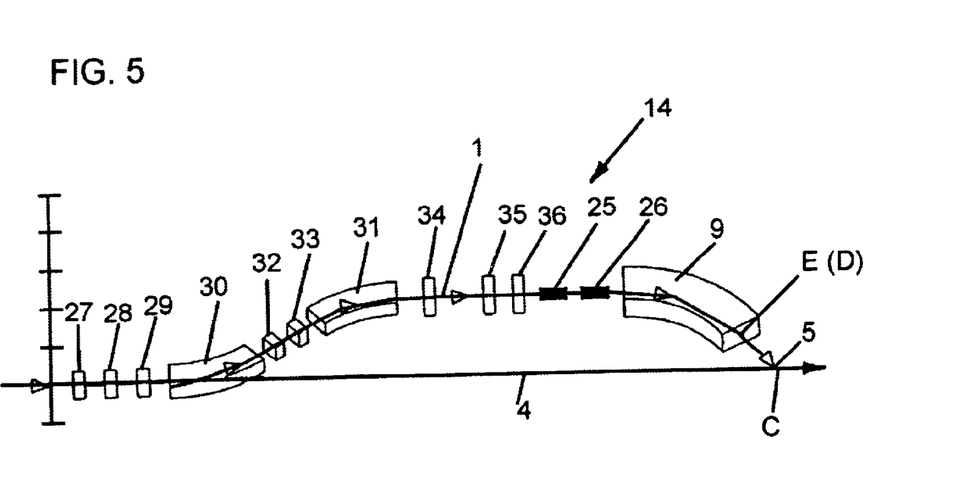
FIG. 5 shows the ion beam guidance of the gantry when α=45°.

FIG. 5 shows the same construction as FIG. 4 with the same components for guidance of the ion beam at an angle α of 45°. In that respect identical elements are referred to in FIG. 5 using identical reference symbols.

Figure 6:
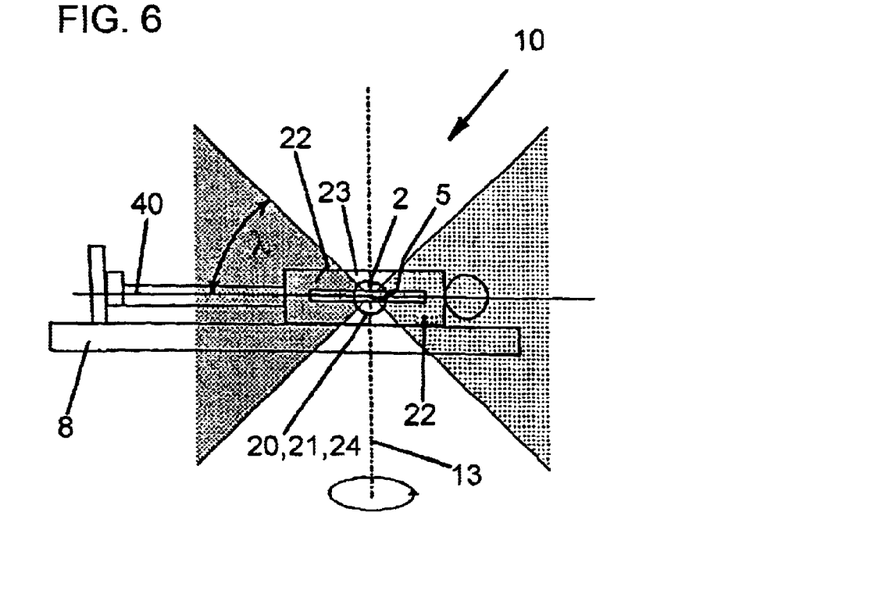
FIG. 6 is a side view of one of the two positions of the target carrier.

FIG. 6 shows a side view of one of the two possible positions of the target carrier 8. The target carrier 8 is arranged in FIG. 6 in a horizontal plane and can be rotated about a vertical axis 13. The target carrier carries a patient 40 having a tumour volume 20. The patient is arranged on the horizontal target carrier of a patient couch or a patient table so that the vertical carrier rotation axis 13 passes through the tumour volume 20, and the target carrier 8 is brought into the isocentre 5 of the gantry system by means of the target carrier system so that the tumour volume 20 is located in the isocentre 5.

Figure 7:
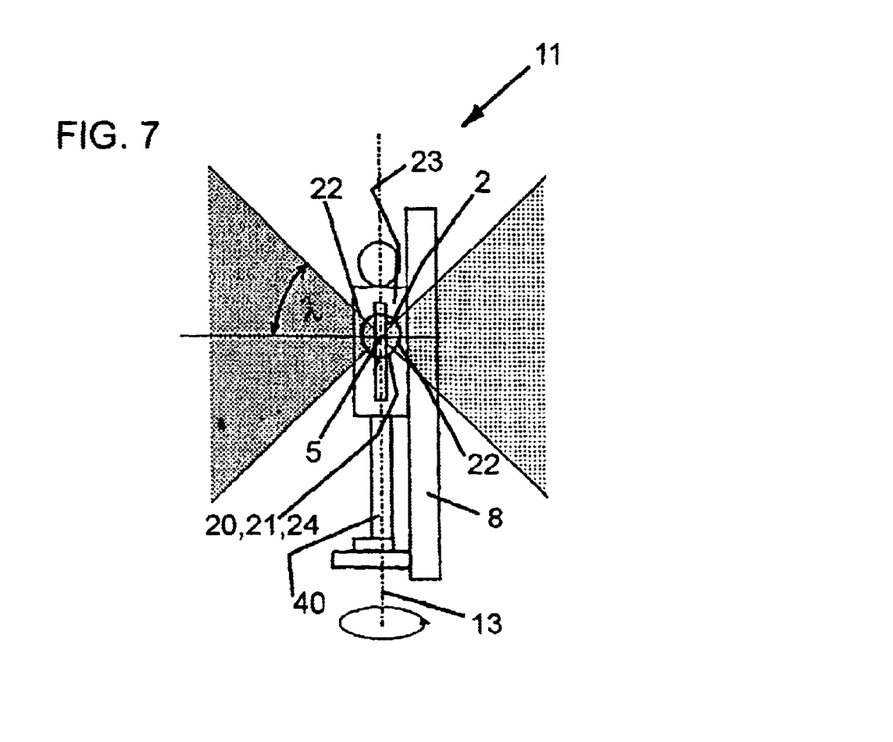
FIG. 7 is a side view of the other of the two positions of the target carrier.

FIG. 6 shows, as dotted areas, the regions that can be achieved as effective treatment angles in a preferred embodiment of the invention by means of position 10 of the target carrier, whereas FIG. 7 shows the second position of the target carrier 8 and indicates, by means of dotted areas, the further regions of a possible effective treatment angle of an embodiment of the gantry system according to the invention.

FIGS. 6 and 7 clearly differentiate, in diagrammatic form, between healthy tissue 22 through which radiation is to pass, unaffected surrounding tissue 23 and the tumour tissue 24 to be irradiated. The dotted areas of FIGS. 6 and 7 are drawn for a deflection angle of 45° and clearly show that, even in the case of such a small deflection angle of the final deflection magnet as 45°, it is possible to adjust and align an ion beam onto a target from freely determinable effective treatment angles.

Figure 8:
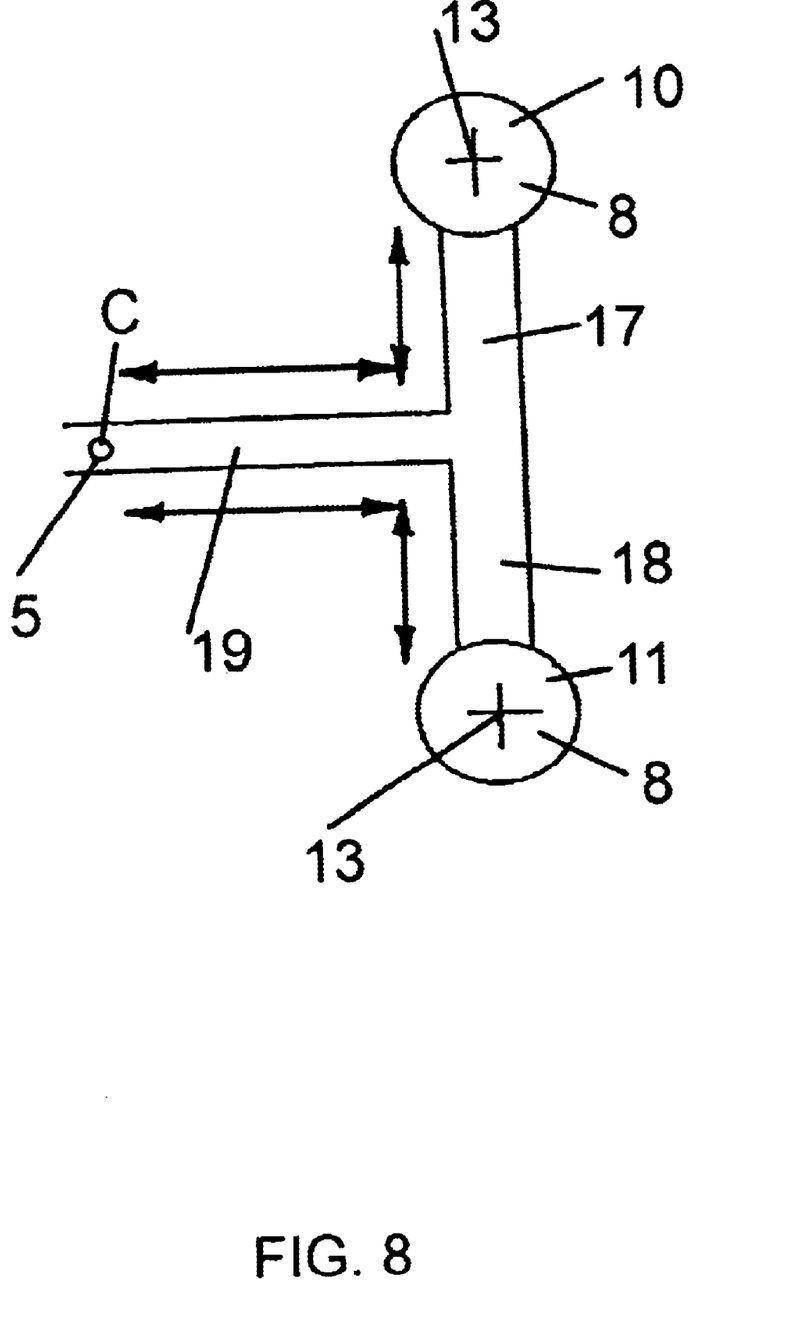
FIG. 8 shows an arrangement of delivery rails according to a further embodiment of the invention.

FIG. 8 shows an arrangement of delivery rails 17, 18 and 19 according to a further embodiment of the invention. Opposite one another on the two delivery rails 17 and 18 there are arranged a target carrier 8 in a first position 10, wherein the target carrier is aligned horizontally, and a target carrier 8 in a further position 11, wherein the target carrier is aligned vertically. The target carriers can, in each case, be rotated about their vertical axes 13.

After the most advantageous effective treatment angle for irradiating a tumour volume has been determined, a patient can be arranged in a required position 10 or 11 of the target carrier 8. The target carrier 8 having the correct position 10 or 11 is then moved on one of the two delivery rails 17 or 18, first up to a central delivery rail 19 and then along the delivery rail 19 towards the isocentre 5 of the gantry system so that the carrier rotation axis of the suitable target carrier is positioned in the isocentre of the gantry system.

Alignment and adjustment of the target carrier 8 by rotating the target carrier 8 about its carrier rotation axis 13 for the most advantage entry channel can be carried out before or after movement into the isocentre 5. Alignment and adjustment of the gantry by rotating the gantry about its horizontal gantry rotation axis for the most advantageous treatment angle can likewise be carried out before or after movement of the patient on the target carrier into the isocentre. Only when adjustment of the suitable treatment angle and entry channel has been completed by selecting the correct position of a target carrier 8 and rotating the target carrier about its carrier rotation axis 13 as well as by rotating the gantry about its horizontal gantry rotation axis can spatial scanning of the entire tumour volume by the ion beam be carried out.

What is claimed is:

1. A gantry system for adjusting and aligning an ion beam (1) onto a target (2) from a freely determinable effective treatment angle, wherein the ion beam (1) is supplied to the gantry system (6) in the horizontally arranged gantry rotation axis (4) and firstly is deflected away from the gantry rotation axis (4) by means of magnetic optics and then is arranged to be so aligned onto a target (2) at adjustable angles of from 0 to 360° around the gantry rotation axis (4) that the ion beam (1) intersects the gantry rotation axis (4) in the isocentre (5) of the gantry system (6), the gantry system (6) having a gantry (14) and a target carrier system (7) which has a rotatable target carrier (8), the carrier rotation axis (13) of which is arranged in the isocentre in a vertical direction with respect to the gantry rotation axis (4), wherein the final deflection magnet (9) so deflects the ion beam (1) that it intersects the gantry rotation axis (4) in the isocentre (5) at an angle of between greater than or equal to 45° and less than 90°, so that the ion beam (1) describes a surface of a cone on rotation of the gantry (14) through a full revolution about the gantry rotation axis (4), wherein the carrier rotation axis (13) of the target carrier (8) can be brought onto the isocentre (5) of the gantry system (6), and wherein the target carrier system (7) has a revolving platform (15), which is rotatable about a vertical revolving platform axis (16), on which two target carriers (8) are arranged in two positions (10, 11), which are perpendicular to one another in a vertical plane, and each of which is rotatable about a vertical carrier rotation axis (13).

2. Gantry system according to claim 1, characterised in that the final deflection magnet (9) so deflects the ion beam (1) that the ion beam (1) intersects the gantry rotation axis (4) at an angle greater than or equal to 45° and less than 90°.

3. Gantry system according to claim 1, characterized in that the vertical carrier rotation axes (13) of the two positions (10, 11) of the target carriers (8) are arranged to be brought alternately into the isocentre (5) of the gantry system (6) by means of a revolving platform (15) as a result of rotation about a revolving platform axis (16).

4. A gantry system for adjusting and aligning an ion beam (1) onto a target (2) from a freely determinable effective treatment angle, wherein the ion beam (1) is supplied to the gantry system (6) in the horizontally arranged gantry rotation axis (4) and firstly is deflected away from the gantry rotation axis (4) by means of magnetic optics and then is arranged to be so aligned onto a target (2) at adjustable angles of from 0 to 360° around the gantry rotation axis (4) that the ion beam (1) intersects the gantry rotation axis (4) in the isocentre (5) of the gantry system (6), the gantry system (6) having a ganry (14) and a target carrier system (7) which has a rotatable target carrier (8), the carrier rotation axis (13) of which is arranged in the isocentre in a vertical direction with respect to the gantry rotation axis (4), wherein the final deflection magnet (9) so deflects the ion beam (1) that it intersects the gantry rotation axis (4) in the isocentre (5) at an angle of between greater than or equal to 45° and less than 90°, so that the ion beam (1) describes a surface of a cone on rotation of the gantry (14) through a full revolution about the gantry rotation axis (4), and the target carrier system (7) has two positions (10, 11) for a target carrier (8), which positions are perpendicular to one another in a vertical plan wherein the carrier rotation axis (13) of the target carrier (8) can be brought into the isocentre (5) of the gantry system (6), and wherein the target carrier system (7) has two separate delivery rails (17, 18), on each of which there is arranged one target carrier (8) of the two positions (10, 11), the delivery rails (17, 18) being capable of laterally displacing, from different directions in each case, either of the target carrires (8) with its carrier rotation axis (13) into the isocentre (5) alternately.

5. A gantry system for adjusting and aligning an ion beam (1) onto a target (2) from a freely determinable effective treatment angle, wherein the ion beam (1) is supplied to the gantry system (6) in the horizontally arranged gantry rotation axis (4) and firstly is deflected away from the gantry rotation axis (4) by means of magnetic optics and then is arranged to be so aligned onto a target (2) at adjustable angles of from 0 to 360° around the gantry rotation axis (4) that the ion beam (1) intersects the gantry rotation axis (4) in the isocentre (5) of the gantry system (6), the gantry system (6) having a gantry (14) and a target carrier system (7) which has a rotatable target carrier (8), the carrier rotation axis (13) of which is arranged in the isocentre in a vertical direction with respect to the gantry rotation axis (4), wherein the final deflection magnet (9) so deflects the ion beam (1) that it intersects the gantry rotation axis (4) in the isocentre (5) at an angle of between greater than or equal to 45° and less than 90°, so that the ion beam (1) describes a surface of a cone on rotation of the gantry (14) through a full revolution about the gantry rotation axis (4), and the target carrier system (7) has two positions (10, 11) for a target carrier (8), which positions are perpendicular to one another in a vertical plane, wherein the carrier rotation axis (13) of the target carrier (8) can be brought into the isocentre (5) of the gantry system (6), and wherein the carrier system (7) has a universal robot system (19), which arranges the target carrier (8) in the two positions (10, 11) and arranges the vertical carrier rotation axis (13) in the isocentre (5).

6. Method for irradiating a tumour from freely determinable effective treatment angles by means of a gantry system (6) according to claim 1, characterized by the following method steps:

determining the most advantageous effective treatment angle and the most advantageous entry channel with respect to the location and size of a tumour (21) in healthy tissue (22) and with the requirement for minimum exposure of the surrounding tissue (23) to radiation and optimum distribution of an ion beam dose for the tumour tissue (24) to be irradiated, selecting, from two target carrier positions (10, 11) located perpendicular to one another in a vertical plane, the target carrier (8) position required for the determined effective treatment angle, bringing the carrier rotation axis (13) of the selected position (10, 11) of the target carrier (8) into the isocentre (5) of the gantry system (6), aligning and adjusting the target carrier (8) by rotation of the target carrier (8) about its vertical carrier rotation axis (13) in respect of the most advantageous entry angle, aligning and adjusting the gantry (14) by rotation of the gantry (14) about its horizontal gantry rotation axis (4) in respect of the most advantageous treatment angle, spatially scanning the entire tumour volume (20), by means of the ion beam (1), from the treatment angle adjusted for the ion beam (1) and through the entry channel adjusted.

* * * * *